United States Patent
Ho

(10) Patent No.: US 11,674,951 B2
(45) Date of Patent: Jun. 13, 2023

(54) METHODS FOR IDENTIFYING A TREATMENT FOR RHEUMATOID ARTHRITIS

(71) Applicant: The Brigham and Women's Hospital, Inc., Boston, MA (US)

(72) Inventor: I-Cheng Ho, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/631,790

(22) PCT Filed: Jul. 17, 2018

(86) PCT No.: PCT/US2018/042485
§ 371 (c)(1),
(2) Date: Jan. 16, 2020

(87) PCT Pub. No.: WO2019/018394
PCT Pub. Date: Jan. 24, 2019

(65) Prior Publication Data
US 2020/0209220 A1 Jul. 2, 2020

Related U.S. Application Data

(60) Provisional application No. 62/533,568, filed on Jul. 17, 2017, provisional application No. 62/613,296, filed on Jan. 3, 2018.

(51) Int. Cl.
*G01N 33/00* (2006.01)
*G01N 33/50* (2006.01)

(52) U.S. Cl.
CPC ... *G01N 33/5023* (2013.01); *G01N 2800/102* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | |
|---|---|---|
| 9,714,937 B2 | 7/2017 | Dunaway |
| 2011/0293643 A1 | 12/2011 | Wilkes |
| 2013/0071860 A1 | 3/2013 | Hale et al. |
| 2016/0024572 A1 | 1/2016 | Shishkin et al. |
| 2016/0042120 A1 | 2/2016 | Danaher |
| 2017/0002405 A1 | 1/2017 | Merritt et al. |

OTHER PUBLICATIONS

Aletaha et al., "The Simplified Disease Activity Index (SDAI) and the Clinical Disease Activity Index (CDAI): a review of their usefulness and validity in rheumatoid arthritis." Clinical and experimental rheumatology, Sep. 2005, 23(5):S100.

Breedveld, et al., "The PREMIER study: a multicenter, randomized, double-blind clinical trial of combination therapy with adalimumab plus methotrexate versus methotrexate alone or adalimumab alone in patients with early, aggressive rheumatoid arthritis who had not had previous methotrexate treatment," Arthritis & Rheumatology, Jan. 2006, 54(1):26-37.

Burmester et al., "Managing rheumatic and musculoskeletal diseases—past, present and future." Nature Reviews Rheumatology, Jul. 2017, 13(7):443-448.

Burmester et al., "Novel treatment strategies in rheumatoid arthritis." The Lancet, Jun. 2017, 389(10086):2338-2348.

Chang et al., "A molecular signature of preclinical rheumatoid arthritis triggered by dysregulated PTPN22," JCI Insight, Oct. 2016, 1(17):e90045, 13 pages.

Cohen et al., "Rituximab for rheumatoid arthritis refractory to anti-tumor necrosis factor therapy: results of a multicenter, randomized, double-blind, placebo-controlled, phase III trial evaluating primary efficacy and safety at twenty-four weeks." Arthritis & Rheumatology, Sep. 2006, 54(9):2793-2806.

Cohen et al., "Treatment of rheumatoid arthritis with anakima, a recombinant human interleukin-1 receptor antagonist, in combination with methotrexate: Results of a twenty-four-week, multicenter, randomized, double-blind, placebo-controlled trial." Arthritis & Rheumatology, Mar. 2002, 46(3):614-624.

Currey et al., "Comparison of azathioprine, cyclophosphamide, and gold in treatment of rheumatoid arthritis." Br. Med. J., Sep. 1974, 3(5934):763-766.

Genovese et al., "Abatacept for rheumatoid arthritis refractory to tumor necrosis factor α inhibition." New England Journal of Medicine, 353(11):1114-1123.

Gibofsky, "Overview of epidemiology, pathophysiology, and diagnosis of rheumatoid arthritis," The American Journal of Managed Care, Dec. 2012, 18(13 Suppl):S295-S302.

Jones et al., "Comparison of tocilizumab monotherapy versus methotrexate monotherapy inpatients with moderate to severe rheumatoid arthritis: the AMBITION study." Annals of the rheumatic diseases, Jan. 2010, 69(01):88-96.

Keystone et al., "Golimumab, a human antibody to TNF-α given by monthly subcutaneous injections, in active rheumatoid arthritis despite methotrexate: the GO-FORWARD Study." Annals of the rheumatic diseases, Jun. 2009, 68(6):789-796.

Klareskog et al., "Therapeutic effect of the combination of etanercept and methotrexate compared with each treatment alone in patients with rheumatoid arthritis: double-blind randomised controlled trial," The Lancet, Feb. 2004, 363(9410):675-681.

Kulkarni, "Digital multiplexed gene expression analysis using the NanoString nCounter system." Current Protocols in Molecular Biology, Apr. 2011, 94(1):25B,10.1-25B.10.17.

Lipsky et al., "Infliximab and methotrexate in the treatment of rheumatoid arthritis." New England Journal of Medicine, Nov. 2000, 343(22):1594-1602.

Malkov et al., "Multiplexed measurements of gene signatures in different analytes using the Nanostring nCounter Assay System," BMC research notes 2, Dec. 2009, 2(1):80, 9 pages.

Moreland et al., "Etanercept Therapy in Rheumatoid Arthritis—A Randomized, Controlled Trial," Annals of internal medicine, Mar. 1999, 130(6)478-486.

(Continued)

*Primary Examiner* — G. R. Ewoldt
(74) *Attorney, Agent, or Firm* — Fish & Richardson P.C.

(57) ABSTRACT

The disclosure relates to biomarkers of rheumatoid arthritis, e.g., PTPN22, PFKFB3, ATM, IL-17A, and IL-17F, and methods of using these biomarkers for selecting an effective treatment for rheumatoid arthritis.

7 Claims, 8 Drawing Sheets

(56) References Cited

OTHER PUBLICATIONS

Nandi et al., "Disease-modifying antirheumatic drugs other than methotrexate in rheumatoid arthritis and seronegative arthritis." Current opinion in rheumatology, May 2008, 20(3):251-256.

O'Dell et al., "Treatment of rheumatoid arthritis with methotrexate alone, sulfasalazine and hydroxychloroquine, or a combination of all three medications." New England Journal of Medicine, May 1996, 334(20):4287-1291.

Smolen et al. "Efficacy and safety of certolizumab pegol plus methotrexate in active rheumatoid arthritis: the RAPID 2 study. A randomised controlled trial." Annals of the rheumatic diseases, Jun. 2009, 68(6):797-804.

Smolen, et al., "Efficacy and safety of leflunomide compared with placebo and sulphasalazine in rheumatoid arthritis: a double-blind, randomised, multicentre trial.," The Lancet, Jan. 1999, 353(9149):259-266.

Smolen, et al., "Proposal for a new nomenclature of disease-modifying antirheumatic drugs," Annals of the Rheumatic Diseases, Jan. 2014, 73(1): 3-5.

Spurlock et al., "Methotrexate Inhibits NF-kB Activity Via Long Intergenic (Noncoding) RNA-p21 Induction," Arthritis & Rheumatology, Nov. 2014, 66(11):2947-2957.

Tugwell et al., "Low-dose cyclosporine versus placebo in patients with rheumatoid arthritis." The Lancet, May 1990, 335(8697):1051-1055.

Vollenhoven et al., "Tofacitinib or adalimumab versus placebo in rheumatoid arthritis," New England Journal of Medicine, Aug. 2012, 367(6):508-519.

CDAI: clinical disease activity index
ΔCDAI= CDAI before treatment – CDAI 12 weeks after treatment; the higher, the better response Measure PFKFB3 and ATM on Enbrel and Humira users
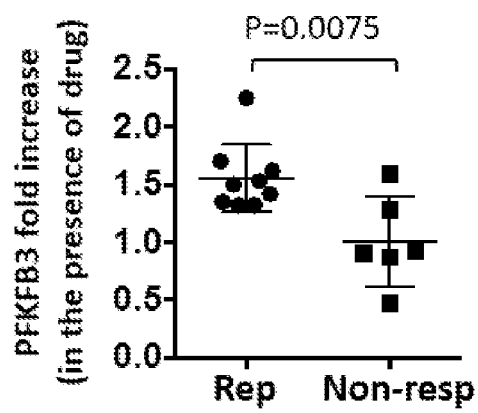 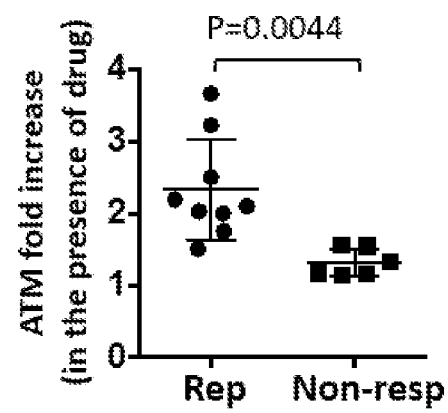
FIG. 7A
FIG. 7B

METHODS FOR IDENTIFYING A TREATMENT FOR RHEUMATOID ARTHRITIS

CROSS REFERENCE TO RELATED APPLICATIONS

This application is a national stage application of PCT/US2018/042485, filed Jul. 17, 2018, which claims the benefit of priority of U.S. Application No. 62/533,568, filed Jul. 17, 2017; and U.S. Application No. 62/613,296, filed Jan. 3, 2018. The content of each of the foregoing applications is hereby incorporated by reference in its entirety.

STATEMENT OF FEDERALLY SPONSORED RESEARCH

This invention was made with government support under Grant no. AR064850 awarded by the National Institutes of Health. The Government has certain rights in the invention.

TECHNICAL FIELD

This disclosure relates to biomarkers of rheumatoid arthritis and methods of treating rheumatoid arthritis.

BACKGROUND

Rheumatoid arthritis (RA) is a long-term autoimmune disorder that primarily affects joints. It typically affects the wrist and hands, with the same joints typically involved on both sides of the body. In some patients, the condition also can damage a wide variety of body systems, including the skin, eyes, lungs, heart and blood vessels.

Rheumatoid arthritis affects more than 1.3 million Americans, and is the most common form of autoimmune arthritis. About 75% of RA patients are women. In fact, 1-3% of women may get rheumatoid arthritis in their lifetime. Disease-modifying antirheumatic drugs (DMARDs) can be used to try to slow down the progression of rheumatoid arthritis. However, a patient may respond to certain DMARDs but not to the others, and ineffective DMARD treatments may cause serious side effects. Accordingly, a more effective way for treating rheumatoid arthritis is urgently required.

SUMMARY

The disclosure relates to methods of treating rheumatoid arthritis.

In one aspect, the disclosure relates to methods of treating a subject having rheumatoid arthritis (RA) or reducing the risk of a subject of developing rheumatoid arthritis. The methods involve contacting a sample comprising peripheral blood mononuclear cells (PBMCs) or T cells collected from the subject with an anti-CD3 antibody in the presence of a disease-modifying antirheumatic drug (DMARD); measuring the expression or transcript levels of one or more RA-related genes selected from the group consisting of PTPN22, PFKFB3, and ATM; determining that the expression or transcript levels of the one or more RA-related genes are above a reference value; and treating the subject with the DMARD.

In some embodiments, the one or more RA-related genes comprises PTPN22. In some embodiments, the one or more RA-related genes comprises PFKFB3. In some embodiments, the one or more RA-related genes comprises ATM.

In some embodiments, the reference value is the value of the expression or transcript levels of the one or more RA-related genes in PBMCs or T cells after being stimulated by the anti-CD3 antibody in the absence of the DMARD.

In some embodiments, the DMARD is a synthetic DMARD or a biologic DMARD. In some embodiments, the DMARD is etanercept, adalimumab, tofacitinib, baricitinib methotrexate, tocilizumab, sarilumab, golimumab, infliximab, certolizumab, or abatacept.

In some embodiments, the subject is a human.

In another aspect, the disclosure relates to methods of treating a subject having rheumatoid arthritis (RA) or reducing the risk of a subject of developing rheumatoid arthritis. The methods involve contacting a sample comprising peripheral blood mononuclear cells (PBMCs) or T cells collected from the subject with an anti-CD3 antibody in the presence of a DMARD; measuring the expression or transcript levels of one or more RA-related genes selected from the group consisting of IL-17A, and IL-17F; determining that the expression or transcript levels of the one or more RA-related genes are below a reference value; and treating the subject with the DMARD.

In some embodiments, the reference value is the value of the expression or transcript levels of the one or more RA-related genes in PBMCs or T cells after being stimulated by the anti-CD3 antibody in the absence of the DMARD.

In some embodiments, the DMARD is a synthetic DMARD or a biologic DMARD.

In another aspect, the disclosure relates to methods of treating a subject having rheumatoid arthritis (RA) or reducing the risk of a subject of developing rheumatoid arthritis. The methods involve contacting a sample comprising peripheral blood mononuclear cells (PBMCs) or T cells collected from the subject with an anti-CD3 antibody in the presence of a DMARD; measuring the expression or transcript levels of one or more RA-related genes selected from the group consisting of PTPN22, PFKFB3, ATM, IL-17A, and IL-17F; determining that one or more expression or transcript level ratios selected from the group consisting of PTPN22/IL-17A, PFKFB3/IL-17A, ATM/IL-17A, PTPN22/IL-17F, PFKFB3/IL-17F, and ATM/IL-17F is greater than a reference ratio value; and treating the subject with the DMARD.

In some embodiments, the reference ratio value is the value of PTPN22/IL-17A, PFKFB3/IL-17A, ATM/IL-17A, PTPN22/IL-17F, PFKFB3/IL-17F, or ATM/IL-17F in PBMCs or T cells after being stimulated by the anti-CD3 antibody in the absence of the DMARD.

In some embodiments, the DMARD is a synthetic DMARD or a biologic DMARD.

In one aspect, the disclosure relates to in vitro methods of determining whether a subject has rheumatoid arthritis (RA) or is at risk of developing rheumatoid arthritis. The methods involve contacting a sample comprising peripheral blood mononuclear cells (PBMCs) or T cells collected from the subject with an anti-CD3 antibody; measuring the expression or transcript levels of one or more RA-related genes selected from the group consisting of PTPN22, PFKFB3, and ATM; comparing the expression or transcript levels of the one or more RA-related genes to a reference value; determining that the expression or transcript levels of the one or more RA-related genes are below the reference value; and identifying the subject as having rheumatoid arthritis or as being at risk of developing rheumatoid arthritis.

In some embodiments, the one or more RA-related genes comprises PTPN22. In some embodiments, the one or more RA-related genes comprises PFKFB3. In some embodiments, the one or more RA-related genes comprises ATM.

In some embodiments, the reference value is the value of the expression or transcript levels of the one or more RA-related genes in PBMCs or T cells from a subject who is not at risk of developing rheumatoid arthritis.

In some embodiments, the subject is a human.

In one aspect, the disclosure provides in vitro methods of determining whether a subject has rheumatoid arthritis (RA) or is at risk of developing rheumatoid arthritis. The methods involve contacting a sample comprising peripheral blood mononuclear cells (PBMCs) or T cells collected from the subject with an anti-CD3 antibody; measuring the expression or transcript levels of one or more RA-related genes selected from the group consisting of IL-17A and IL-17F; comparing the expression or transcript levels of the one or more RA-related genes to a reference value; determining that the expression or transcript levels of the one or more RA-related genes are above the reference value; and identifying the subject as having rheumatoid arthritis or as being at risk of developing rheumatoid arthritis.

In some embodiments, the reference value is the value of the expression or transcript levels of the one or more RA-related genes in PBMCs or T cells from a subject who is not at risk of developing rheumatoid arthritis.

In another aspect, the disclosure provides in vitro methods of determining whether a subject has rheumatoid arthritis (RA) or is at risk of developing rheumatoid arthritis. The methods involve contacting a sample comprising peripheral blood mononuclear cells (PBMCs) or T cells collected from the subject with an anti-CD3 antibody; measuring the expression or transcript levels of one or more RA-related genes selected from the group consisting of PTPN22, PFKFB3, ATM, IL-17A and IL-17F; determining that one or more expression or transcript level ratios selected from the group consisting of PTPN22/IL-17A, PFKFB3/IL-17A, ATM/IL-17A, PTPN22/IL-17F, PFKFB3/IL-17F, and ATM/IL-17F is below a reference ratio; and identifying the subject as having rheumatoid arthritis or as being at risk of developing rheumatoid arthritis.

In some embodiments, the reference ratio is the value of PTPN22/IL-17A, PFKFB3/IL-17A, ATM/IL-17A, PTPN22/IL-17F, PFKFB3/IL-17F, or ATM/IL-17F in PBMCs or T cells from a subject who is not at risk of developing rheumatoid arthritis.

In one aspect, the disclosure provides methods of identifying a compound for treating rheumatoid arthritis. The methods involve contacting a sample comprising peripheral blood mononuclear cells (PBMCs) or T cells collected from a subject with an anti-CD3 antibody in the presence of a test compound; measuring the expression or transcript levels of one or more RA-related genes selected from the group consisting of PTPN22, PFKFB3, and ATM; determining that the expression or transcript levels of the one or more RA-related genes are above a reference value; and identifying the test compound as a compound for treating rheumatoid arthritis.

In some embodiments, the subject has rheumatoid arthritis. In some embodiments, the subject is at risk of developing rheumatoid arthritis.

In some embodiments, the reference value is the value of the expression or transcript levels of the one or more RA-related genes in PBMCs or T cells before being stimulated by the anti-CD3 antibody.

In some embodiments, the reference value is the value of the expression or transcript levels of the one or more RA-related genes in PBMCs or T cells after being stimulated by the anti-CD3 antibody in the absence of the test compound.

In some embodiments, the one or more RA-related genes comprises PTPN22. In some embodiments, the one or more RA-related genes comprises PFKFB3. In some embodiments, the one or more RA-related genes comprises ATM.

In some embodiments, the test compound is an antibody or a small molecule. In some embodiments, the test compound is etanercept, adalimumab, tofacitinib, baricitinib methotrexate, tocilizumab, sarilumab, golimumab, infliximab, certolizumab, or abatacept.

In one aspect, the disclosure relates to methods of identifying a compound for treating rheumatoid arthritis. The methods involve contacting a sample comprising peripheral blood mononuclear cells (PBMCs) or T cells collected from a subject with an anti-CD3 antibody in the presence of a test compound; measuring the expression or transcript levels of one or more RA-related genes selected from the group consisting of IL-17A and IL-17F; determining that the expression or transcript levels of the one or more RA-related genes are below a reference value; and identifying the test compound as a compound for treating rheumatoid arthritis.

In some embodiments, the subject has rheumatoid arthritis or the subject is at risk of developing rheumatoid arthritis.

In some embodiments, the reference value is the value of the expression or transcript levels of the one or more RA-related genes in PBMCs or T cells before being stimulated by the anti-CD3 antibody.

In some embodiments, the reference value is the value of the expression or transcript levels of the one or more RA-related genes in PBMCs or T cells after being stimulated by the anti-CD3 antibody in the absence of the test compound.

In one aspect, the disclosure relates to methods of identifying a compound for treating rheumatoid arthritis. The methods involve contacting peripheral blood mononuclear cells (PBMCs) or T cells collected from a subject with an anti-CD3 antibody in the presence of a test compound; measuring the expression or transcript levels of one or more RA-related genes selected from the group consisting of PTPN22, PFKFB3, ATM, IL-17A and IL-17F; determining that that one or more expression or transcript level ratios selected from the group consisting of PTPN22/IL-17A, PFKFB3/IL-17A, ATM/IL-17A, PTPN22/IL-17F, PFKFB3/IL-17F, and ATM/IL-17F is greater than a reference ratio; and identifying the test compound as a compound for treating rheumatoid arthritis.

In some embodiments, the subject has rheumatoid arthritis or the subject is at risk of developing rheumatoid arthritis.

In some embodiments, the reference ratio is the value of PTPN22/IL-17A, PFKFB3/IL-17A, ATM/IL-17A, PTPN22/IL-17F, PFKFB3/IL-17F, or ATM/IL-17F in PBMCs or T cells before being stimulated by the anti-CD3 antibody.

In some embodiments, the reference ratio is the value of PTPN22/IL-17A, PFKFB3/IL-17A, ATM/IL-17A, PTPN22/IL-17F, PFKFB3/IL-17F, or ATM/IL-17F in PBMCs or T cells after being stimulated by the anti-CD3 antibody in the absence of the test compound.

In one aspect, the disclosure relates to methods that involve the steps of contacting peripheral blood mononuclear cells (PBMCs) collected from a subject with an anti-CD3 antibody; and measuring the expression or transcript levels of one or more RA-related genes selected from the group consisting of PTPN22, PFKFB3, ATM, IL-17A and IL-17F.

In some embodiments, the one or more RA-related genes comprises PTPN22. In some embodiments, the one or more RA-related genes comprises PFKFB3. In some embodiments, the one or more RA-related genes comprises ATM.

In some embodiments, the expression or transcript levels of the one or more RA-related genes are measured by RT-PCR. In some embodiments, the expression or transcript levels of the one or more RA-related genes are measured by RNA sequencing, NanoString, or RNA microarray. In some embodiments, the expression or transcript levels of the one or more RA-related genes are measured by ELISA, cell cytometry, or western blot.

In some embodiments, the subject has rheumatoid arthritis or is suspected of having rheumatoid arthritis. In some embodiments, the subject is at risk of developing rheumatoid arthritis.

In some embodiments, the PMBCs are stimulated with the anti-CD3 antibody in the presence of a DMARD.

In some embodiments, the DMARD is a fusion protein, an antibody, or a small molecule.

In another aspect, the disclosure provides methods of determining whether a treatment of rheumatoid arthritis to a subject is effective. The methods involve contacting a sample comprising peripheral blood mononuclear cells (PBMCs) or T cells collected from the subject with an anti-CD3 antibody, wherein the subject is under the treatment of rheumatoid arthritis; measuring the expression or transcript levels of one or more RA-related genes selected from the group consisting of PTPN22, PFKFB3, ATM; determining that the expression or transcript levels of the one or more RA-related genes are above a reference value; and continuing treating the subject with the treatment.

In some embodiments, the reference value is the expression or transcript levels of the one or more RA-related genes in PBMCs after anti-CD3 antibody stimulation before the treatment.

In some embodiments, the reference value is the expression or transcript levels of the one or more RA-related genes in PBMCs after anti-CD3 antibody stimulation in healthy subjects.

In some embodiments, the one or more RA-related genes comprises PTPN22. In some embodiments, the one or more RA-related genes comprises PFKFB3. In some embodiments, the one or more RA-related genes comprises ATM.

In another aspect, the disclosure relates to methods of determining whether a treatment of rheumatoid arthritis to a subject is effective. The methods involve contacting a sample comprising peripheral blood mononuclear cells (PBMCs) or T cells collected from the subject with an anti-CD3 antibody, wherein the subject is under the treatment of rheumatoid arthritis; measuring the expression or transcript levels of one or more RA-related genes selected from the group consisting of IL-17A and IL-17F; determining that the expression or transcript levels of the one or more RA-related genes are below a reference value; and continuing treating the subject with the treatment.

In some embodiments, the reference value is the expression or transcript levels of the one or more RA-related genes in PBMCs after anti-CD3 antibody stimulation before the treatment.

In some embodiments, the reference value is the expression or transcript levels of the one or more RA-related genes in PBMCs after anti-CD3 antibody stimulation in healthy subjects.

In another aspect, the disclosure relates to methods of determining whether a treatment of rheumatoid arthritis to a subject is effective. The methods involve contacting a sample comprising peripheral blood mononuclear cells (PBMCs) or T cells collected from the subject with an anti-CD3 antibody, wherein the subject is under the treatment of rheumatoid arthritis; measuring the expression or transcript levels of one or more RA-related genes selected from the group consisting of PTPN22, PFKFB3, ATM, IL-17A and IL-17F; determining that one or more expression or transcript level ratios selected from the group consisting of PTPN22/IL-17A, PFKFB3/IL-17A, ATM/IL-17A, PTPN22/IL-17F, PFKFB3/IL-17F, and ATM/IL-17F is greater than a reference ratio; and continuing treating the subject with the treatment.

In some embodiments, the reference ratio is the value of PTPN22/IL-17A, PFKFB3/IL-17A, ATM/IL-17A, PTPN22/IL-17F, PFKFB3/IL-17F, or ATM/IL-17F in PBMCs or T cells after anti-CD3 antibody stimulation before the treatment.

In some embodiments, the reference ratio is the value of PTPN22/IL-17A, PFKFB3/IL-17A, ATM/IL-17A, PTPN22/IL-17F, PFKFB3/IL-17F, or ATM/IL-17F in PBMCs or T cells after anti-CD3 antibody stimulation in healthy subjects.

In another aspect, the disclosure relates to methods of determining whether a treatment of rheumatoid arthritis (RA) to a subject is effective. The methods involve contacting a sample comprising peripheral blood mononuclear cells (PBMCs) or T cells collected from the subject with an anti-CD3 antibody at a first time point; measuring first expression or transcript levels of one or more RA-related genes selected from the group consisting of PTPN22, PFKFB3, ATM; treating the subject with a treatment for rheumatoid arthritis; contacting PBMCs or T cells collected from the subject with an anti-CD3 antibody at a second time point; measuring second expression or transcript levels of the one or more RA-related genes; determining that the second expression or transcript levels of the one or more RA-related genes are higher than the first expression or transcript levels of the one or more RA-related genes; and continuing treating the subject with the treatment.

In some embodiments, the one or more RA-related genes comprises PTPN22. In some embodiments, the one or more RA-related genes comprises PFKFB3. In some embodiments, the one or more RA-related genes comprises ATM.

In another aspect, the disclosure relates to methods of determining whether a treatment of rheumatoid arthritis (RA) to a subject is effective. The methods involve contacting peripheral blood mononuclear cells (PBMCs) or T cells collected from the subject with an anti-CD3 antibody at a first time point; measuring first expression or transcript levels of one or more RA-related genes selected from the group consisting of IL-17A and IL-17F; treating the subject with a treatment for rheumatoid arthritis; contacting PBMCs or T cells collected from the subject with an anti-CD3 antibody at a second time point; measuring second expression or transcript levels of the one or more RA-related genes; determining that the second expression or transcript levels of the one or more RA-related genes are lower than the first expression or transcript levels of the one or more RA-related genes; and continuing treating the subject with the treatment.

In one aspect, the disclosure also provides methods of determining whether a treatment of rheumatoid arthritis (RA) to a subject is effective. The methods involve contacting a sample comprising peripheral blood mononuclear cells (PBMCs) or T cells collected from the subject with an anti-CD3 antibody at a first time point; measuring the expression or transcript levels of one or more RA-related genes selected from the group consisting of PTPN22, PFKFB3, ATM, IL-17A and IL-17F; determining a first expression or transcript level ratio selected from the group consisting of PTPN22/IL-17A, PFKFB3/IL-17A, ATM/IL-17A, PTPN22/IL-17F, PFKFB3/IL-17F, and ATM/IL-17F; treating the subject with a treatment for rheumatoid arthritis; contacting PBMCs or T cells collected from the subject with an anti-CD3 antibody at a second time point; measuring expression or transcript levels of the one or more RA-related genes; determining a second expression or transcript level ratio; determining that the second ratio is higher than the first ratio; and continuing treating the subject with the treatment.

In one aspect, the disclosure relates to methods of predicting patients at risk for developing rheumatoid arthritis (RA) or clinically presenting with RA. The methods involve the steps of (a) collecting peripheral blood mononuclear cells (PBMCs) or T cells (e.g., CD4+ T cells) from the patients; (b) stimulating in vitro the collected cells with an anti-CD3 challenge; (c) measuring the expression or transcript levels of one or more of several genes in response to the anti-CD3 antibody challenge; (d) comparing the expression of one or more of the genes wherein the expression of one or more of the genes will be altered in RA patients or the patients in at risk for developing RA relative to the expression of said genes in patients not at risk for developing RA; and (e) making a clinical decision or intervention based on the results of the measurement/comparison of the expression.

In some embodiments, one or more of several genes are selected from PTPN22, PFKFB3, ATM, IL-17A and IL-17F.

In some embodiments, the transcript expression and/or level of these genes (e.g., PTPN22, PFKFB3, ATM), in response to an anti-CD3 antibody challenge, is impaired or decreased in patients at risk for developing rheumatoid arthritis (RA) relative to patients not at risk for developing rheumatoid arthritis (RA).

In some embodiments, the transcript expression and/or level of these genes (e.g., IL-17A and IL-17F), in response to an anti-CD3 antibody challenge, is significantly increased in patients at risk for developing rheumatoid arthritis (RA) as compared to patients not at risk for developing rheumatoid arthritis (RA).

In one aspect, the disclosure relates to methods of predicting the clinical response of a patient to anti-RA drugs or compounds. The methods involve the steps of (a) providing or collecting a sample comprising peripheral blood mononuclear cells (PBMCs) or T cells (e.g., CD4+ T cells) from patients with active RA; (b) stimulating in vitro the collected cells with an anti-CD3 antibody challenge either in the presence or absence of an anti-RA drug/compound or a combination of anti-RA drugs/compounds; (c) measuring the expression or transcript levels of one or more of several genes by the anti-CD3 antibody challenged-cells in the presence or absence of the anti-RA drug/compound or combination of said anti-RA drugs/compounds; (d) comparing the ability of an anti-RA drug/compound to normalize the expression of one or more of said genes to an anti-CD3 challenge wherein the ability of the anti-RA drug/compound to normalize said expression predicts the clinical effectiveness of the anti-RA drug/compound for the said patient.

In some embodiments, one or more of several genes are selected from PTPN22, PFKFB3, A TM, IL-I 7 A and IL-I 7F. In some embodiments, the anti-RA drug is selected from etanercept (ENBREL®) and adalimumab (HUMIRA®).

In another aspect, the disclosure relates to methods of screening for novel anti-RA drugs/compounds. The methods involve the steps of collecting peripheral blood mononuclear cells (PBMCs) or T cells from patients with active RA; (b) stimulating in vitro the collected cells with an anti-CD3 challenge either in the presence or absence of said new drug/compound; (c) measuring the expression or transcript levels of one or more of several genes by the anti-CD3 challenged-PBMCs in the presence or absence of said new drug/compound; (d) comparing the ability of said new drug/compound to normalize the expression of one or more of said genes to an anti-CD3 antibody challenge wherein the ability of said anti-RA drug to normalize said expression predicts a potential clinical use of said drug/compound to treat RA.

In some embodiments, one or more of several genes are selected from PTPN22, PFKFB3, ATM, IL-17A, and IL-17F.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 7A. Anti-CD3 antibody mediated induction of PFKFB3 in PBMCs from responders to etanercept (ENBREL®) and non-responders to etanercept (ENBREL®).

FIG. 7B. Anti-CD3 antibody mediated induction of ATM in PBMC from responders to adalimumab (HUMIRA®) and non-responders to adalimumab (HUMIRA®).

DETAILED DESCRIPTION

Figure 1:
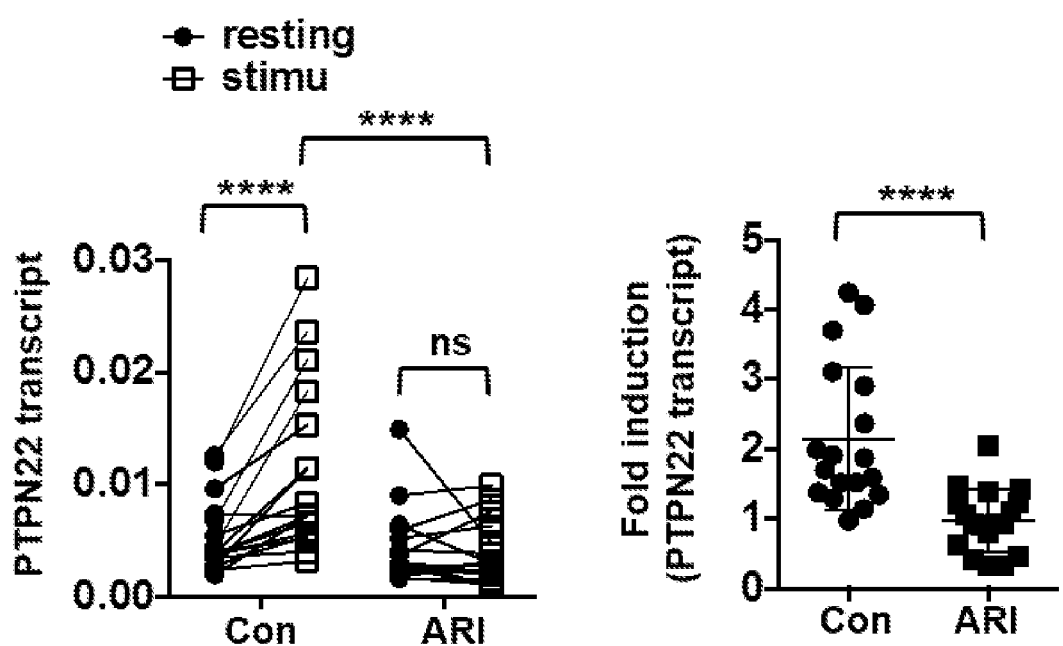
FIG. 1. Impaired anti-CD3 antibody mediated induction of PTPN22 in PBMC from at-risk individuals (ART).

Rheumatoid arthritis is a chronic disease that causes joint pain, stiffness, swelling and decreased movement of the joints. Small joints in the hands and feet are most commonly affected. Many therapeutic agents are available for treating rheumatoid arthritis (RA) (e.g., disease modifying antirheumatic drugs (DMARDs)). However, a subject may respond to certain DMARDs but not to the others. The present disclosure provides methods of determining whether a patient is likely to respond to DMARDs.

Peripheral blood mononuclear cells (PBMC) from RA patients and healthy but at risk individuals have aberrant expression of several genes, including PTPN22, PFKFB3, ATM, IL-17A, and IL-17F, in response to anti-CD3 antibody stimulation. Anti-CD3 monoclonal antibodies can induce lymphocytes (e.g., T cells) to proliferate, and induce profound gene expression change. For example, anti-CD3 antibody stimulation can increase the level of PTPN22 transcript by approximately 2 fold in healthy not-at-risk individuals, but no induction (1 fold) is often detected in RA or at-risk individuals. This abnormal gene expression pattern can be corrected or normalized after an effective treatment.

The present disclosure also shows that PBMCs can be taken from RA patients and stimulated with anti-CD3 antibody for 24 hours in the absence or presence of the DMARDs; the effectiveness of the DMARDs in normalizing the expression of PTPN22, PFKFB3, ATM, IL-17A, and/or IL-17F can predict patient's response to the DMARDs. For example, if a DMARD can increase the transcript level of PTPN22, PFKFB3, or ATM by near 2 folds after anti-CD3 antibody stimulation of PBMCs obtained from a given patient, then this DMARD is effective for treating rheumatoid arthritis in this patient. Reversely, if a DMARD is unable to efficiently increase the transcript level of PTPN22, PFKFB3, or ATM (e.g., less than 1.5 fold), then it is likely that this drug is ineffective for the patient.

With respect to IL-17A and IL-17F, these two genes have higher expression level in patients with RA or in at-risk individuals than healthy not-at-risk individuals. If a DMARD cannot decrease the transcript level of IL-17A or IL-17F in RA patients after anti-CD3 antibody stimulation of PMBC, thus cannot normalize the transcript level of these two genes, then it is likely that the DMARD is ineffective for the patient.

Rheumatoid Arthritis (RA)

Rheumatoid arthritis is a chronic inflammatory joint disease, which can cause cartilage and bone damage as well as disability. RA typically results in warm, swollen, and painful joints. Pain and stiffness often worsen following rest. Other signs and symptoms that can occur in RA include, e.g., loss of energy, low fevers, loss of appetite, dry eyes and mouth, Sjögren's syndrome, and firm lumps, which grow beneath the skin in places such as the elbow and hands (rheumatoid nodules).

The cause of rheumatoid arthritis involves a combination of genetic and environmental factors. The underlying mechanism involves the body's immune system attacking the joints. This results in inflammation and thickening of the joint capsule. It also affects the underlying bone and cartilage. The diagnosis is made mostly on the basis of a person's signs and symptoms. X-rays and laboratory testing may support a diagnosis or exclude other diseases with similar symptoms. Early diagnosis is key to optimal therapeutic success, particularly in patients with well-characterized risk factors for poor outcomes such as high disease activity, presence of autoantibodies, and early joint damage.

Treatment usually involves measuring disease and the use of synthetic or biological disease-modifying antirheumatic drugs (DMARDs). After the treatment target of stringent remission (or at least low disease activity) is maintained, dose reduction can be attempted.

The Clinical Disease Activity Index (CDAI) is a useful clinical composite score for patients with rheumatoid arthritis. In some embodiments, it can be determined by the following formula:

$$CDAI=SJC(28)+TJC(28)+PGA+EGA,$$

wherein SJC(28) is Swollen 28-Joint Count (shoulders, elbows, wrists, MCPs, PIPs including thumb IP, knees), TJC(28) is Tender 28-Joint Count (shoulders, elbows, wrists, MCPs, PIPs including thumb IP, knees), PGA is Patient Global disease Activity (patient's self assessment of overall RA disease activity on a scale 1-10 where 10 is maximal activity), and EGA is Evaluator's Global disease Activity (evaluator's assessment of overall RA disease activity on a scale 1-10 where 10 is maximal activity). In some embodiments, a subject with an RA can have a CDAI that is equal to or greater than 5, 10, 15, or 20. In some embodiments, the subject has an active RA, and a subject with an active RA can have a CDAI that is equal to or greater than 10. A CDAI that is equal to or greater than 10 often indicates moderate or severe RA.

A detailed description regarding CDAI can be found, e.g., in Aletaha et al., "The Simplified Disease Activity Index (SDAI) and the Clinical Disease Activity Index (CDAI): a review of their usefulness and validity in rheumatoid arthritis." Clinical and experimental rheumatology 23.5 (2005): S100, which is incorporated herein by reference in its entirety. General background regarding rheumatoid arthritis and methods of diagnosing and treating rheumatoid arthritis can be found, e.g., Gibofsky, "Overview of epidemiology, pathophysiology, and diagnosis of rheumatoid arthritis," The American journal of managed care 18.13 Suppl (2012): S295-302, which is incorporated herein by reference in its entirety.

Disease-Modifying Antirheumatic Drugs (DMARDs)

Disease-modifying antirheumatic drugs (DMARDs) is a category of drugs defined by their use in rheumatoid arthritis to slow down disease progression. The term is often used in contrast to nonsteroidal anti-inflammatory drug (which refers to agents that treat the inflammation but not the underlying cause) and steroids (which blunt the immune response but are not ideal for long-term treatment because of many serious side effects).

DMARDs inhibit joint damage, suppress the acute phase response, decrease autoantibody levels and exert effects on long-term functional outcome beyond those on signs and symptoms alone, as conveyed merely by symptomatic drugs. Because DMARDs target the disease process, they are less likely to have serious side effects.

The common DMARDs include e.g., synthetic DMARDs and biological DMARDs. As used herein, the term "synthetic DMARD" or "chemical DMARD" refers to DMARDs that are chemically synthesized, e.g., small molecule DMARDS. As used herein, the term "biological DMARD" refers to a DMARD that is derived from or made from a living organism, e.g., proteins, fusion proteins, or antibodies. A detailed description regarding various DMARDs can be found, e.g., in Smolen, et al., "Proposal for a new nomenclature of disease-modifying antirheumatic drugs," Annals of the rheumatic diseases 73.1 (2014): 3-5; and Nandi et al., "Disease-modifying antirheumatic drugs other than methotrexate in rheumatoid arthritis and seronegative arthritis." Current opinion in rheumatology 20.3 (2008): 251-256; Burmester et al., "Managing rheumatic and musculoskeletal diseases—past, present and future." Nature Reviews Rheumatology (2017); Burmester et al., "Novel treatment strategies in rheumatoid arthritis." The Lancet 389.10086 (2017): 2338-2348; each of which is incorporated herein by reference in its entirety.

Synthetic DMARDs

The most common synthetic DMARDs include, e.g., methotrexate, sulfasalazine, hydroxychloroquine, leflunomide, gold salts, azathioprine, apremilast, and cyclosporine. Among them, methotrexate, sulfasalazine, hydroxychloroquine, and leflunomide are more commonly used.

Methotrexate (MTX), also known as amethopterin, is a chemotherapy agent and immune system suppressant. It was originally used as a chemotherapy treatment for cancer. When used in much lower doses for rheumatoid arthritis and other rheumatic diseases, methotrexate works to reduce inflammation and to decrease joint damage. It is usually taken once per week as a pill, liquid, or injection. Common side effects include upset stomach and a sore mouth. Methotrexate can interfere with the bone marrow's production of blood cells. Low blood cell counts can cause fever, infections, swollen lymph nodes, and easy bruisability and bleeding. Liver or lung damage can occur, even with low doses, and therefore requires monitoring.

Sulfasalazine is a medication that is often used to treat rheumatoid arthritis, ulcerative colitis, and Crohn's disease. Particularly, it is often considered as a first line treatment in rheumatoid arthritis. Sulfasalazine is usually started at a low dose and is increased slowly to minimize side effects. Side effects of sulfasalazine include changes in blood counts, nausea or vomiting, sensitivity to sunlight, skin rash, and headaches.

Hydroxychloroquine was originally developed as a treatment for malaria, and was later found to improve symptoms of arthritis. It can be used early in the course of rheumatoid arthritis and is often used in combination with other DMARDs. It is also very frequently used for treatment of systemic lupus erythematosus. It can be combined with steroid medications to reduce the amount of steroid needed. Taking a high dose of hydroxychloroquine for prolonged periods of time may increase the risk of damage to the retina of the eye, although high doses are not usually required for treatment of rheumatoid conditions or lupus. Thus, an eye examination by an ophthalmologist is recommended before starting treatment and periodically thereafter.

Leflunomide inhibits production of inflammatory cells to reduce inflammation. It is a pyrimidine synthesis inhibitor that works by inhibiting dihydroorotate dehydrogenase. It is often used alone but may be used in combination with methotrexate for people who have not responded adequately to methotrexate alone or together with a biologic agent. Side effects of leflunomide include rash, temporary hair loss, liver damage, nausea, diarrhea, weight loss, and abdominal pain. Testing for prior exposure to hepatitis and regular blood testing while on therapy are needed to monitor for liver damage and other toxicities.

Azathioprine has been used in the treatment of cancer, rheumatoid arthritis, lupus, and a variety of other inflammatory illnesses. Azathioprine is generally reserved for patients who have not responded to other RA treatments. The most common side effects of azathioprine include nausea, vomiting, decreased appetite, liver function abnormalities, low white blood cell counts, and infection.

Cyclosporine was originally developed to prevent rejection after organ transplantation. It works in patients with rheumatoid arthritis to inhibit T lymphocytes, a cell that contributes to the inflammation associated with rheumatoid arthritis. There is concern about the long-term safety of cyclosporine and its association with kidney disease and high blood pressure, so it is generally reserved for patients who have not responded to other RA treatments. Side effects of cyclosporine include high blood pressure, gum swelling, kidney damage, increased hair growth, nausea, diarrhea, and heartburn.

Another group of DMARDs, called kinase inhibitors, includes, e.g., tofacitinib and baricitinib. Tofacitinib and baricitinib are synthetic DMARD. They are drugs of the janus kinase (JAK) inhibitor class, and are currently approved for the treatment of rheumatoid arthritis.

Various synthetic DMARDs are known in the field, and a detailed description of these synthetic DMARDs and methods of using them are described, e.g., in Klareskog, et al., "Therapeutic effect of the combination of etanercept and methotrexate compared with each treatment alone in patients with rheumatoid arthritis: double-blind randomised controlled trial," The Lancet 363.9410 (2004): 675-681; O'Dell et al., "Treatment of rheumatoid arthritis with methotrexate alone, sulfasalazine and hydroxychloroquine, or a combination of all three medications." New England Journal of Medicine 334.20 (1996): 1287-1291; Smolen, et al., "Efficacy and safety of leflunomide compared with placebo and sulphasalazine in rheumatoid arthritis: a double-blind, randomised, multicentre trial.," The Lancet 353.9149 (1999): 259-266; Currey et al., "Comparison of azathioprine, cyclophosphamide, and gold in treatment of rheumatoid arthritis." Br Med J 3.5934 (1974): 763-766; Tugwell et al., "Low-dose cyclosporine versus placebo in patients with rheumatoid arthritis." The Lancet 335.8697 (1990): 1051-1055; van Vollenhoven, et al., "Tofacitinib or adalimumab versus placebo in rheumatoid arthritis," New England Journal of Medicine 367.6 (2012): 508-519; each of which is incorporated herein by reference in its entirety.

Biologic DMARDs

Another class of medications used in persons with rheumatoid arthritis and related inflammatory rheumatic conditions is biologic agents, sometimes called biologic DMARDs (in contrast to the conventional or traditional synthetic DMARDs or nonbiologic DMARDs). Biologics target molecules on cells of the immune system, joints, and the products that are secreted in the joints, all of which can cause inflammation and joint destruction. There are several types of biologics, each of which targets a specific type of molecule involved in this process.

Biologics that bind tumor necrosis factor (TNF) include etanercept (ENBREL®), adalimumab (HUMIRA®), infliximab (REMICADE®), certolizumab pegol (CIMZIA®), and golimumab (SIMPONI®). These are called anti-TNF agents or TNF inhibitors.

There are additional biologics that target other molecules instead of TNF. These DMARDs target a variety of other agents with different targets (e.g., interleukin 1 (IL1) receptor, CD20, CD80, CD86, or interleukin-6 receptor). These DMARDs include e.g., anakinra, abatacept, rituximab, sarilumab, and tocilizumab. Among them, anakinra is an interleukin 1 (IL1) receptor antagonist. Abatacept is a fusion protein composed of the Fc region of the immunoglobulin IgG1 fused to the extracellular domain of CTLA-4. Rituximab is an antibody that targets CD20. Tocilizumab is a humanized monoclonal antibody against the interleukin-6 receptor (IL-6R), and sarilumab is a human monoclonal antibody against IL-6R.

Unlike synthetic DMARDs (with the exception of tofacitinib and baricitinib), which can take a month or more to begin working, biologic DMARDs tend to work rapidly, within two weeks for some medications and within four to six weeks for others. Biologics can be used alone or in combination with other DMARDs (e.g., methotrexate), Nonsteroidal Anti-inflammatory Drugs (NSAIDs), and/or glucocorticoids (steroids).

In some embodiments, biological DMARDs are used for people who have not completely responded to synthetic DMARDs and for those who cannot tolerate synthetic DMARDs in doses large enough to control inflammation. Biologic agents are usually administered by injection. Some can be injected under the skin or can be injected into a vein.

Various biologic DMARDs are known in the field, and a detailed description of these biologic DMARDs and methods of using them can be found, e.g., in Moreland et al, "Etanercept Therapy in Rheumatoid Arthritis-A Randomized, Controlled Trial," Annals of internal medicine 130.6 (1999): 478-486; Breedveld, et al., "The PREMIER study: a multicenter, randomized, double-blind clinical trial of combination therapy with adalimumab plus methotrexate versus methotrexate alone or adalimumab alone in patients with early, aggressive rheumatoid arthritis who had not had previous methotrexate treatment," Arthritis & Rheumatology 54.1 (2006): 26-37; Lipsky, et al. "Infliximab and methotrexate in the treatment of rheumatoid arthritis." New England Journal of Medicine 343.22 (2000): 1594-1602; Smolen, et al. "Efficacy and safety of certolizumab pegol plus methotrexate in active rheumatoid arthritis: the RAPID 2 study. A randomised controlled trial." Annals of the rheumatic diseases 68.6 (2009): 797-804; Keystone, et al. "Golimumab, a human antibody to TNF-α given by monthly subcutaneous injections, in active rheumatoid arthritis despite methotrexate: the GO-FORWARD Study." Annals of the rheumatic diseases (2008); Cohen, et al. "Treatment of rheumatoid arthritis with anakinra, a recombinant human interleukin-1 receptor antagonist, in combination with methotrexate: Results of a twenty-four-week, multicenter, randomized, double-blind, placebo-controlled trial." Arthritis & Rheumatology 46.3 (2002): 614-624; Genovese, et al. "Abatacept for rheumatoid arthritis refractory to tumor necrosis factor α inhibition." New England Journal of Medicine 353.11 (2005): 1114-1123; Cohen, et al. "Rituximab for rheumatoid arthritis refractory to anti-tumor necrosis factor therapy: results of a multicenter, randomized, double-blind, placebo-controlled, phase III trial evaluating primary efficacy and safety at twenty-four weeks." Arthritis & Rheumatology 54.9 (2006): 2793-2806; Jones et al. "Comparison of tocilizumab monotherapy versus methotrexate monotherapy in patients with moderate to severe rheumatoid arthritis: the AMBITION study." Annals of the rheumatic diseases 69.01 (2010): 88-96; each of which is incorporated herein by reference in its entirety.

Gene Expression and Rheumatoid Arthritis

The disclosure provides gene expression profile in a biological sample from subjects with rheumatoid arthritis or at risk of developing rheumatoid arthritis. In some embodiments, the biological sample comprises or consists essentially of peripheral blood mononuclear cells. In some embodiments, the biological sample comprises or consists essentially of T cells (e.g., purified T cells, or CD4+ T cells). In some embodiments, the sample is isolated and/or derived from whole blood, lymph, or bone marrows.

As used herein, the term "peripheral blood mononuclear cell" or "PBMC" refers to peripheral blood cells having a round nucleus. These cells include, e.g., lymphocytes (e.g., T cells, B cells, NK cells) and monocytes, and are characterized by one round nucleus. Samples comprising PBMCs or lymphocytes (e.g., T cells, B cells, NK cells) can be obtained from a subject according to any methods known in the art. Generally, a sample that is isolated and/or derived from a subject and suitable for being assayed for PBMCs expression profile analysis can be used in the methods as described herein. In some embodiments, the PMBCs are freshly isolated PBMCs or cryopreserved PBMCs (e.g., PBMCs that have been cryopreserved for more than 1 day, 2 days, 5 days, 1 week, 1 month, or 1 year).

PBMCs and T cells can be extracted from samples (e.g., whole blood) by various methods known in the art. For example, PBMCs can be extracted from whole blood by using gradient centrifugation which can separate the blood into a top layer of plasma, followed by a layer of PBMCs and a bottom fraction of polymorphonuclear cells (such as neutrophils and eosinophils) and erythrocytes. In some embodiments, a hydrophilic polysaccharide (e.g., ficoll) that can separate layers of blood can also be used. In some embodiments, the polymorphonuclear cells can be further isolated by lysing the red blood cells.

Expression and/or transcript levels of genes in PBMCs or T cells can be determined by various methods known in the art, e.g., real time PCR, quantitative PCR, microarrays (e.g., RNAmicroarrays), northern blot, RNA-sequencing, or NanoString assays (e.g., gene expression panel or nCounter™ Assay). In some embodiments, cell cytometry, immunoassay methods (e.g., western blot or basic enzyme-linked immunosorbent assay (ELISA)) or other methods can also be used to determine the expression level of genes. In some embodiments, high throughput methods, e.g., protein or gene chips, can be used. Some of these methods are described, e.g., in US20170002405; US20160042120; U.S. Pat. No. 9,714,937; Malkov, Vladislav A, et al. "Multiplexed measurements of gene signatures in different analytes using the Nanostring nCounter Assay System." BMC research notes 2 (2009): 80-80; Kulkarni, Meghana M. "Digital multiplexed gene expression analysis using the NanoString nCounter system." Current Protocols in Molecular Biology (2011): 25B-10; each of which is incorporated by reference in its entirety.

Anti-CD3 monoclonal antibodies can induce lymphocytes (e.g., T cells) to proliferate, and induce profound gene expression change. The present disclosure shows that in response to anti-CD3 antibody stimulation, peripheral blood mononuclear cells (PBMC) or T cells from (1) RA patients and (2) healthy but at risk individuals have aberrant expression of several RA-related genes. As used herein, the term "RA-related gene" refers to a gene that has different expression pattern in healthy subjects and subjects with RA (or subjects who are at risk of developing RA).

The RA-related genes include e.g., Protein tyrosine phosphatase non-receptor 22 (PTPN22; NM_001193431.2→NP_001180360.1), 6-phosphofructo-2-kinase/fructose-2,6-bisphosphatase 3 (PFKFB3; NM_001145443.2→NP 001138915.1), Ataxia Telangiectasia Mutated (ATM or ATM Serine/Threonine Kinase; NM_000051.3→NP_000042.3), Interleukin 17A (IL-17A; NM_002190.2→NP_002181.1), and Interleukin 17F (IL-17F; NM_052872.3→NP_443104.1). These RA-related genes can have abnormally high expression in RA patients or at risk individuals (e.g., PTPN22, PFKFB3, or ATM), or abnormally low expression in RA patients or at risk individuals (e.g., IL-17A or IL-17F) after anti-CD3 antibody stimulation.

The present disclosure has determined that the expression or transcript level of PTPN22, PFKFB3, or ATM in samples collected from healthy subjects increases more than the sample collected from subjects with RA after anti-CD3 antibody stimulation. In contrast, the expression or transcript level of IL-17A or IL-17F in samples collected from subjects with RA increases more than the sample collected from healthy subjects after anti-CD3 antibody stimulation.

The change of the expression level can be compared to the expression profile of a biological sample before the anti-CD3 antibody stimulation. In some embodiments, anti-CD3 antibody stimulation can increase the expression or transcript level of a RA-related gene more than 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.5 fold, 4.0 fold, 4.5 fold, 5 fold, 6 fold, 7 fold, 8 fold, 9 fold, 10 fold, 15 fold, or 20 fold in samples (e.g., PBMCs or T cells).

In some embodiments, anti-CD3 antibody stimulation can increase the expression or transcript level of a RA-related gene no more than 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.5 fold, 4.0 fold, 4.5 fold, 5 fold, 6 fold, 7 fold, 8 fold, 9 fold, 10 fold, 15 fold, or 20 fold in samples (e.g., PBMCs or T cells).

The expression or transcript level of PTPN22, PFKFB3, or ATM after anti-CD3 antibody stimulation in samples (e.g., PBMCs or T cells) collected from healthy subjects, subjects who are not at risk of developing RA, subjects with low risk of developing RA, or RA patients who have received an effective treatment for RA can be at least 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.5 fold, 4.0 fold, 4.5 fold, 5 fold, 6 fold, 7 fold, 8 fold, 9 fold, 10 fold, 15 fold, or 20 fold higher than a reference value. In some embodiments, the reference value is the expression or transcript level of a RA-related gene after anti-CD3 antibody stimulation in samples (e.g., PBMCs or T cells) collected from subjects with RA, subjects who are at risk of developing RA, or RA patients who have not received an effective treatment for RA. In some embodiments, the reference value is the expression or transcript level of a RA-related gene in samples (e.g., PBMCs or T cells) before anti-CD3 antibody stimulation.

In contrast, the expression or transcript level of IL-17A or IL-17F after anti-CD3 antibody stimulation in samples (e.g., PBMCs or T cells) collected from subjects with RA, subjects who are at risk of developing RA, or RA patients who have not received an effective treatment for RA is higher than the expression or transcript level in samples collected from healthy subjects. In some embodiments, the expression or transcript level is at least 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.5 fold, 4.0 fold, 4.5 fold, 5 fold, 6 fold, 7 fold, 8 fold, 9 fold, 10 fold, 15 fold, or 20 fold higher than a normal reference value (or healthy reference value). In some embodiments, the normal reference value is the expression or transcript level of a RA-related gene after anti-CD3 antibody stimulation in samples (e.g., PBMCs or T cells) collected from healthy subjects, subjects who are not at risk of developing RA, subjects with low risk of developing RA, or RA patients who have received an effective treatment for RA.

Therefore, the present disclosure provides methods of determining whether a subject have RA, whether a subject is at risk of developing RA, or whether a subject is in need of preventive treatment of RA. In some embodiments, the methods involve collecting a sample (e.g., PBMCs or T cells) from the subject; stimulating the sample with an anti-CD3 antibody; measuring the expression or transcript levels of one or more of RA-related genes; and comparing the expression or transcript levels of the one or more RA-related genes to a reference value. The reference value can be the expression or transcript levels of the RA-related genes in a sample before anti-CD3 antibody stimulation, the expression or transcript levels of the RA-related genes in a sample of subjects who are healthy and are not at risk of developing RA, the expression or transcript levels of the RA-related genes in a sample of subjects who have RA, or the expression or transcript levels of the RA-related genes in a sample of subjects who are at risk of developing RA. In some embodiments, the expression or transcript levels of the RA-related genes are measured before anti-CD3 antibody stimulation. In some embodiments, the expression or transcript levels of the RA-related genes are measured after anti-CD3 antibody stimulation.

A suitable reference value can be determined by many methods known in the art. In some embodiments, the reference value is the expression or transcript levels of the RA-related genes in a sample (e.g., PBMCs or T cells) before anti-CD3 antibody stimulation.

In some embodiments, if the expression or transcript levels of PTPN22, PFKFB3, or ATM in PBMCs or T cells after anti-CD3 antibody stimulation is above the reference value (e.g., greater than 1.2 fold, 1.5 fold, 2.0 fold, or 2.5 fold of the reference value), then the subject is not likely to have RA, or the subject is not at risk of developing RA, otherwise the subject is likely to have RA or is at risk of developing RA. In some embodiments, the reference value is the expression or transcript levels of PTPN22, PFKFB3, or ATM after anti-CD3 antibody stimulation in PBMCs or T cells of subjects who are healthy and are not at risk of developing RA. If the expression or transcript levels of the RA-related genes in PBMCs or T cells after anti-CD3 antibody stimulation is below the reference value (e.g., less than 0.5 fold, 0.6 fold, 0.7, 0.8 fold, 0.9 fold of the reference value), then it indicates that the anti-CD3 antibody stimulation cannot increase the expression of PTPN22, PFKFB3, or ATM to the normal level, thus the subject is likely to have RA, or the subject is at risk of developing RA, otherwise, the subject is not likely to have RA or is not at risk of developing RA.

In some embodiments, the methods as described in the present disclosure involve comparing the expression or transcript levels of one or more of RA-related genes to a reference value. In some embodiments, the expression or transcript levels of one or more of RA-related genes is significantly above a reference value. In some embodiments, the expression or transcript levels of one or more of RA-related genes is significantly below a reference value. In some embodiments, the reference value is the expression or transcript levels of PTPN22, PFKFB3, or ATM after anti-CD3 antibody stimulation in PBMCs or T cells of subjects who have RA or subjects who are at risk of developing RA.

In some embodiments, the reference value is the average or median expression or transcript levels of one or more of RA-related genes of a group of subjects (e.g., the expression or transcript levels of the RA-related genes in samples before anti-CD3 antibody stimulation or the expression or transcript levels of the RA-related genes after anti-CD3 antibody stimulation in samples of subjects who have RA or subjects who are at risk of developing RA). In some embodiments, the reference value is the expression or transcript levels of one or more of RA-related genes determined from a cohort of cells. In some embodiments, the reference value can also be selected to indicate severity, stage, or progression of the RA in the subject.

In some embodiments, the reference value is a threshold as determined empirically or by any other methods known in the art (e.g., by the range or the distribution of expression or transcript levels of the RA-related genes in PBMCs). In some embodiments, the threshold is determined by testing a large number of subjects, and is selected for highest accuracy, highest positive predictive value, highest negative predictive value, highest sensitivity, highest specificity, and/or highest area under the curve (AUC).

Furthermore, as the expression or transcript levels of PTPN22, PFKFB3, and ATM increase more in healthy (not at risk) subjects, and the expression or transcript levels of IL-17A and IL-17F increase more in subjects with RA, the expression or transcript level ratio of these genes can be used to determine whether a subject has rheumatoid arthritis (RA) or is at risk of developing rheumatoid arthritis. In some embodiments, one or more expression or transcript level ratios are selected from the group consisting of PTPN22/IL-17A, PFKFB3/IL-17A, ATM/IL-17A, PTPN22/IL-17F, PFKFB3/IL-17F, and ATM/IL-17F. These ratios can be compared against a reference ratio. The reference ratio can be the value of PTPN22/IL-17A, PFKFB3/IL-17A, ATM/IL-17A, PTPN22/IL-17F, PFKFB3/IL-17F, or ATM/IL-17F in a sample (e.g., PBMCs or T cells) from a subject who is not at risk of developing rheumatoid arthritis after anti-CD3 antibody stimulation. If the ratio is below the reference ratio, then subject is likely to have rheumatoid arthritis or have a risk of developing rheumatoid arthritis. Similarly, if the ratio is equal to or above the reference ratio, the subject is not likely to have rheumatoid arthritis or is not likely to have a risk of developing rheumatoid arthritis.

Methods of Treatment

Rheumatoid arthritis is usually treated by DMARDs. The choice of DMARD depends on a number of factors, including the stage and severity of the joint condition, the balance between possible side effects and expected benefits, and patient preference. Before treatment begins, the patient and clinician can discuss the benefits and risks of each type of therapy, including possible side effects and toxicities, dosing schedule, monitoring frequency, and expected results. However, a subject may respond to certain DMARDs but not the others, thus not all DMARDs are equally effective for a particular subject. The present disclosure shows that for subjects with rheumatoid arthritis, effective DMARDs can change the expression or transcript level of RA-related genes after anti-CD3 antibody stimulation back to normal. The abnormal gene expression pattern can be corrected or normalized after effective treatment. For example, an effective treatment can increase the expression level of PTPN22, PFKFB3, or ATM, or decrease the expression level of IL-17A or IL-17F after anti-CD3 antibody stimulation.

Thus, the methods as described herein can be used to select an effective treatment for a subject with rheumatoid arthritis. Generally, the methods include determining whether a subject is likely to respond to a treatment (e.g., a compound, a combination of compounds, a DMARD, or a combination of DMARDs), and administering the treatment to the subject.

As used in this context, to "treat" means to ameliorate at least one symptom of the disorder associated with rheumatoid arthritis. Often, the treatment results in a relief of joint pain or stiffness. The treatment can also slow the progression of the disease in the subject. Administration of an effective treatment to the subject can also result in normalizing the expression or transcript level of RA-related genes after anti-CD3 antibody stimulation in PMBCs collected from the subject.

The terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals. In some embodiments, the subject is a human (e.g., male human or female human) with an age over 25 years old, 30 years old, 40 years old, 50 years old, 60 years old, 70 years old, or 80 years old.

As used herein, the terms "therapeutically effective" and "effective amount", used interchangeably, applied to a dose or amount refers to a quantity of a composition, compound or pharmaceutical formulation that is sufficient to result in a desired activity upon administration to a subject in need thereof. Within the context of the present disclosure, the term "therapeutically effective" refers to that the composition, compound or pharmaceutical formulation, in a sufficient amount, can reduce or eliminate at least one symptom or one condition of rheumatoid arthritis.

In one aspect, the disclosure provides methods of treating a subject having rheumatoid arthritis (RA) or reducing the risk of a subject of developing rheumatoid arthritis. In some embodiments, the methods involve stimulating a sample (e.g., PBMCs or T cells) collected from the subject with an anti-CD3 antibody in the presence of an agent (e.g., a DMARD) or a combination of agents; measuring the expression or transcript levels of a set of RA-related genes; comparing the expression or transcript levels of the set of RA-related genes against a reference value; and treating the subject with the agent or the combination of agents. In some embodiments, the set of RA-related genes can have 1, 2, 3, 4, 5 or more than 5 RA-related genes. In some embodiments, the set of RA-related genes has only one gene.

The reference value can be any reference value or threshold as described in the present disclosure and can be determined by methods known in the art. In some embodiments, the reference value can be determined in a sample (e.g., PBMCs or T cells) after being stimulated by the anti-CD3 antibody in the absence of an agent (e.g., DMARD) or a combination of agents. If the expression or transcript levels of the set of RA-related genes are significantly different from a reference value (indicating that the expression of RA-related genes has been normalized), the subject is likely to respond to the agent (e.g., a DMARD) or the combination of the agents, otherwise the subject is not likely to respond to the agent or the combination of the agents.

In some embodiments, the reference value is the expression or transcript levels of PTPN22, PFKFB3 or ATM in a sample (e.g., PBMCs or T cells) before anti-CD3 antibody stimulation. If the expression or transcript levels of PTPN22, PFKFB3 or ATM in a sample (e.g., PBMCs or T cells) after anti-CD3 antibody stimulation in the presence of agents (e.g. DMARD) or a combination of agents are above the reference value, the subject is likely to respond to the agent (e.g. a DMARD) or the combination of the agents, otherwise the subject is not likely to respond to the agent or the combination of the agents.

In some embodiments, the reference value is the expression or transcript levels of PTPN22, PFKFB3 or ATM after anti-CD3 antibody stimulation in a sample (e.g., PBMCs or T cells) of subjects who are healthy and are not at risk of developing RA. If the expression or transcript levels of PTPN22, PFKFB3 or ATM in a sample (e.g., PBMCs or T cells) after anti-CD3 antibody stimulation in the presence of agents (e.g. DMARD) or a combination of agents are equal to or are above the reference value, the subject is likely to respond to the agent (e.g. a DMARD) or the combination of the agents, otherwise the subject is not likely to respond to the agent or the combination of the agents.

In some embodiments, the reference value is the expression or transcript levels of PTPN22, PFKFB3 or ATM in a sample (e.g., PBMCs or T cells) after anti-CD3 antibody stimulation before the treatment. If the expression or transcript levels of PTPN22, PFKFB3 or ATM in a sample (e.g., PBMCs or T cells) after anti-CD3 antibody stimulation in the presence of agents (e.g. DMARD) or a combination of agents are above the reference value, the subject is likely to respond to the agent (e.g. a DMARD) or the combination of the agents, otherwise the subject is not likely to respond to the agent or the combination of the agents.

In some embodiments, the methods involve stimulating a sample (e.g., PBMCs or T cells) collected from the subject with an anti-CD3 antibody, wherein the subject is receiving a treatment for rheumatoid arthritis; measuring the expression or transcript levels of PTPN22, PFKFB3 or ATM; determining that the expression or transcript levels of PTPN22, PFKFB3 or ATM are above a reference value; and continuing treating the subject with the treatment. In some embodiments, the reference value can be the expression or transcript levels of PTPN22, PFKFB3 or ATM in a sample (e.g., PBMCs or T cells) after anti-CD3 antibody stimulation before the treatment (e.g., baseline levels). Thus, if the expression or transcript levels of PTPN22, PFKFB3 or ATM are above the reference value (e.g., significantly above the reference value, or greater than 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, or 3.0 fold of the reference value), then the treatment is effective.

In some embodiments, the methods involve measuring the expression or transcript levels of IL-17A or IL-17F; determining that the expression or transcript levels of IL-17A or IL-17F are below a reference value; and continuing treating the subject with the treatment. In some embodiments, the reference value can be the expression or transcript levels of IL-17A or IL-17F in a sample (e.g., PBMCs or T cells) after anti-CD3 antibody stimulation before the treatment (e.g., baseline levels). Thus, if the expression or transcript levels of IL-17A or IL-17F is below (e.g., significantly below) the reference value or less than 0.9, 0.8, 0.7, 0.6, 0.5, 0.4, 0.3, 0.2, or 0.1 of the reference vale, then the treatment is effective.

In some embodiments, the methods involve comparing one or more expression or transcript level ratios, e.g., PTPN22/IL-17A, PFKFB3/IL-17A, ATM/IL-17A, PTPN22/IL-17F, PFKFB3/IL-17F, and ATM/IL-17F, against a reference ratio value. In some embodiments, the reference ratio can be determined in a sample (e.g., PBMCs or T cells) after anti-CD3 antibody stimulation before the treatment (e.g., baseline levels). Thus, if the ratio is above the reference ratio (e.g., significantly above the reference ratio, or greater than 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, or 3.0 fold of the reference ratio), then the treatment is effective.

In some embodiments, the methods involve collecting samples (e.g., PBMCs or T cells) from RA patients, and stimulating the cells with anti-CD3 antibody for 24 hours in the absence or presence of each of one or more DMARDs. The effectiveness of each of the DMARDs in normalizing the expression of PTPN22, PFKFB3, ATM, IL-17A, and IL-17F can predict the patient's response to each of the DMARDs.

Thus, in one aspect, the disclosure provides an assay to predict a patient's response to an agent (e.g., a DMARD) or a combination of agents (e.g., a combination of DMARDs). The prediction can be used to facilitate the clinical decision making process (e.g., reduce dosage of DMARDs or adjust dosage of DMARDs). The methods can also involve splitting PBMC samples collected from a patient; stimulating the PBMC samples with an anti-CD3 antibody in the presence or in the absence of a DMARD; measuring the expression or transcript level of a RA-related gene (e.g., PTPN22). If the presence of the DMARD can normalize the expression or transcript level of the RA-related gene (e.g., PTPN22) in response to the anti-CD3 antibody stimulation, that patient is likely to respond to that DMARD and can be treated with that DMARD.

In some embodiments, PBMC samples collected from a subject can be split to two samples. The first sample is stimulated with an anti-CD3 antibody in the presence of a test agent or a combination of the test agents. The second sample is stimulated with an anti-CD3 antibody in the absence of the test agent or the combination of the test agents. The expression or transcript level of the RA-related gene in the first sample is then divided by the expression or transcript level of the RA-related gene in the second sample. In some embodiments, the ratio is greater than 1 (e.g., greater than 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 4, 5, 6, 7, 8, 9, 10, 15, 20, 25, or 30). In some embodiments, the ratio can be less than a threshold (e.g., 0.5, 0.6, 0.7, 0.8, 0.9, 1.0, 1.1, 1.2, 1.3, 1.4, 1.5, 1.6, 1.7, 1.8, 1.9, or 2.0).

During the treatment, the blood pressure and kidney function can be monitored on a regular basis. Periodic blood tests are also recommended to monitor the blood count on a regular basis. Monitoring reduces the risk of long-term damage from DMARDs. In some embodiments, the treatment can also include one or more DMARDs to improve effectiveness (e.g., more than one DMARD can be used). In some embodiments, nonsteroidal anti-inflammatory drug and/or steroids are also administered to the subject. A patient who does not respond completely to a single DMARD can be given a combination of DMARDs, e.g., methotrexate plus another DMARD. In some embodiments, nonsteroidal anti-inflammatory drug and/or steroids are also administered to the subject to control the symptoms.

The responsiveness to rheumatoid arthritis treatment can be determined by methods known in the art, e.g., by Clinical Disease Activity Index (CDAI). In some embodiments, one or both conditions have to be met to be considered as a responder.

(1). CDAI decrease>=50%;

(2). CDAI decrease>=12 for those with baseline CDAI>22, CDAI decrease>=6 for those with baseline CDAI>=10, CDAI decrease>=1 for those with baseline CDAI<10.

In some embodiments, the first condition is used to determine whether a subject is a responder. In some embodiments, the second condition is used to determine whether a subject is a responder.

The disclosure also provides methods of determining whether a treatment is effective. In some embodiments, the methods involve stimulating a sample (e.g., PBMCs or T cells) collected from the subject with an anti-CD3 antibody, wherein the subject is receiving a treatment for rheumatoid arthritis; measuring the expression or transcript levels of PTPN22, PFKFB3, or ATM; determining that the expression or transcript levels of PTPN22, PFKFB3, or ATM equal to or are above a reference value. In some embodiments, the reference value is the expression or transcript levels of PTPN22, PFKFB3, or ATM in a sample (e.g., PBMCs or T cells) after anti-CD3 antibody stimulation in healthy subjects. If the expression or transcript levels of PTPN22, PFKFB3, or ATM equal to or are above the reference value, it indicates that the treatment has corrected the abnormal expression pattern of the RA-related genes in RA patients after anti-CD3 antibody stimulation, and thus the treatment is effective. In some embodiments, the reference value is the expression or transcript levels of the set of RA-related genes in RA patients who respond to a treatment or RA patients who have been successfully treated. If the expression or transcript levels of a set of RA-related genes equal to or are above the reference value, it also indicates that the treatment is effective.

In some embodiments, the methods involve contacting peripheral blood mononuclear cells (PBMCs) or T cells collected from the subject with an anti-CD3 antibody, wherein the subject is under the treatment of rheumatoid arthritis; measuring the expression or transcript levels of one or more RA-related genes selected from the group consisting of IL-17A and IL-17F; determining that the expression or transcript levels of the one or more RA-related genes are below a reference value; and continuing treating the subject with the treatment.

In some embodiments, the methods involve contacting peripheral blood mononuclear cells (PBMCs) or T cells collected from the subject with an anti-CD3 antibody, wherein the subject is under the treatment of rheumatoid arthritis; measuring the expression or transcript levels of one or more RA-related genes selected from the group consisting of PTPN22, PFKFB3, ATM, IL-17A and IL-17F; determining that one or more expression or transcript level ratios selected from the group consisting of PTPN22/IL-17A, PFKFB3/IL-17A, ATM/IL-17A, PTPN22/IL-17F, PFKFB3/IL-17F, and ATM/IL-17F is greater than a reference ratio; and continuing treating the subject with the treatment.

The disclosure also provides methods of determining whether a treatment is effective by measuring the expression or transcript levels of a set of RA-related genes in multiple time points. In some embodiments, the methods involve stimulating a sample (e.g., PBMCs or T cells) collected from the subject with an anti-CD3 antibody at a first time point; measuring first expression or transcript levels of PTPN22, PFKFB3, or ATM; treating the subject with a treatment for rheumatoid arthritis; stimulating a sample (e.g., PBMCs or T cells) collected from the subject with an anti-CD3 antibody at a second time point; measuring second expression or transcript levels of PTPN22, PFKFB3, or ATM. If the second expression or transcript levels are higher than the first expression or transcript levels, then it indicates that the treatment is effective for the subject, and the subject is continued to be treated by the treatment.

In some embodiments, the methods involve contacting peripheral blood mononuclear cells (PBMCs) or T cells collected from the subject with an anti-CD3 antibody at a first time point; measuring first expression or transcript levels of one or more RA-related genes selected from the group consisting of IL-17A and IL-17F; treating the subject with a treatment for rheumatoid arthritis; contacting PBMCs or T cells collected from the subject with an anti-CD3 antibody at a second time point; measuring second expression or transcript levels of the one or more RA-related genes; determining that the second expression or transcript levels of the one or more RA-related genes are lower than the first expression or transcript levels of the one or more RA-related genes; and continuing treating the subject with the treatment.

In some embodiments, the methods involve contacting peripheral blood mononuclear cells (PBMCs) or T cells collected from the subject with an anti-CD3 antibody at a first time point; measuring the expression or transcript levels of one or more RA-related genes selected from the group consisting of PTPN22, PFKFB3, ATM, IL-17A and IL-17F; determining a first expression or transcript level ratio selected from the group consisting of PTPN22/IL-17A, PFKFB3/IL-17A, ATM/IL-17A, PTPN22/IL-17F, PFKFB3/IL-17F, and ATM/IL-17F; treating the subject with a treatment for rheumatoid arthritis; contacting PBMCs or T cells collected from the subject with an anti-CD3 antibody at a second time point; measuring expression or transcript levels of the one or more RA-related genes; determining a second expression or transcript level ratio; determining that the second ratio is higher than the first ratio; and continuing treating the subject with the treatment.

Screening

The disclosure provides methods of identifying a compound for treating rheumatoid arthritis. In some embodiments, the methods involve PBMCs or T cells collected from one or several RA patients with an anti-CD3 antibody in the presence of a test compound; measuring the expression or transcript levels of a set of RA-related genes; and comparing the expression or transcript levels of the set of RA-related genes to a reference value. If the expression or transcript levels of the set of RA-related genes are significantly different from a reference value, then the test compound is selected as a compound for treating rheumatoid arthritis. The reference value can be the value of the expression or transcript levels of the set of RA-related genes in PBMCs or T cells before being stimulated by the anti-CD3 antibody, or the expression or transcript levels of the set of RA-related genes in PBMCs or T cells after being stimulated by the anti-CD3 antibody in the absence of the test compound.

The assays as described herein can help determine which candidate drug should be brought forward to clinical trials. A candidate compound that can normalize the anti-CD3 antibody induced expression of RA-related genes (e.g., PTPN22) are likely to be effective for treating RA.

In some embodiments, the methods involve contacting peripheral blood mononuclear cells (PBMCs) or T cells collected from a subject with an anti-CD3 antibody in the presence of a test compound; measuring the expression or transcript levels of one or more RA-related genes selected from the group consisting of PTPN22, PFKFB3, and ATM; determining that the expression or transcript levels of the one or more RA-related genes are above a reference value; and identifying the test compound as a compound for treating rheumatoid arthritis.

In some embodiments, the methods involve contacting peripheral blood mononuclear cells (PBMCs) or T cells collected from a subject with an anti-CD3 antibody in the presence of a test compound; measuring the expression or transcript levels of one or more RA-related genes selected from the group consisting of IL-17A and IL-17F; determining that the expression or transcript levels of the one or more RA-related genes are below a reference value; and identifying the test compound as a compound for treating rheumatoid arthritis.

In some embodiments, the methods involve contacting peripheral blood mononuclear cells (PBMCs) or T cells collected from a subject with an anti-CD3 antibody in the presence of a test compound; measuring the expression or transcript levels of one or more RA-related genes selected from the group consisting of PTPN22, PFKFB3, ATM, IL-17A and IL-17F; determining that that one or more expression or transcript level ratios selected from the group consisting of PTPN22/IL-17A, PFKFB3/IL-17A, ATM/IL-17A, PTPN22/IL-17F, PFKFB3/IL-17F, and ATM/IL-17F is greater than a reference ratio; and identifying the test compound as a compound for treating rheumatoid arthritis.

In some embodiments, the subject has rheumatoid arthritis or subject is at risk of developing rheumatoid arthritis.

The test compounds can include, e.g., polypeptides, polynucleotides, inorganic or organic large or small molecule test compounds. These test compounds can be used to identify agents useful in the treatment of rheumatoid arthritis.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can also be, e.g., natural products or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, e.g., Czarnik, Curr. Opin. Chem. Bio. 1:60-6 (1997)). In addition, a number of small molecule libraries are commercially available.

Libraries screened using the methods of the present disclosure can comprise a variety of types of test compounds. A given library can comprise a set of structurally related or unrelated test compounds. In some embodiments, the test compounds are peptide or peptidomimetic molecules. In some embodiments, the test compounds are nucleic acids.

Test compounds identified as "hits" in a first screen can be selected and systematically altered, e.g., using rational design, to optimize binding affinity, avidity, specificity, or other parameter. Such optimization can also be screened for using the methods described herein. Thus, in some embodiments, the disclosure includes screening a first library of compounds using a method known in the art and/or described herein, identifying one or more hits in that library, subjecting those hits to systematic structural alteration to create a second library of compounds structurally related to the hit, and screening the second library using the methods described herein.

A variety of techniques useful for determining the structures of "hits" can be used in the methods described herein, e.g., NMR, mass spectrometry, gas chromatography equipped with electron capture detectors, fluorescence and absorption spectroscopy. Thus, the disclosure also includes compounds identified as "hits" by the methods described herein, and methods for their administration and use in the treatment, prevention, or delay of development or progression of rheumatoid arthritis.

In some embodiments, the test compound is an antibody. The antibody can target any known proteins that are involved in rheumatoid arthritis rheumatoid arthritis pathology. In some embodiments, the antibody can target TNF, IL1, IL-1 receptor, CD20, CD80, CD86, CTLA-4, IL-6, or IL-6 receptor.

Kits

The present disclosure provides kits for use in detecting the expression or transcript levels of RA-related genes, and methods of manufacturing them. In some embodiments, the kits can include necessary devices or agents for collecting PBMCs, and/or performing real time PCR, quantitative PCR, microarrays (e.g., RNA microarrays), northern blot, or RNA-sequencing, immunoassays (e.g., western blot or ELISA).

EXAMPLES

The invention is further described in the following examples, which do not limit the scope of the invention described in the claims.

Example 1: Subjects at Risk of Developing RA have Impaired Induction of PTPN22 in PBMC after Anti-CD3 Antibody Stimulation Blood was collected from healthy subjects who were at risk of developing rheumatoid arthritis (RA) and control subjects. The peripheral blood mononuclear cells (PBMC) in the blood samples were stimulated by anti-CD3 antibodies (LEAF™ Purified anti-human CD3 Antibody, BioLegend, San Diego, Calif., Catalog #300314). The level of PTPN22 transcripts was quantified with RT-PCR.

Healthy subjects who were at risk of developing rheumatoid arthritis had impaired induction of PTPN22 in their PBMC after anti-CD3 stimulation. The level of PTPN22 was induced by 2-fold after 24 hours of anti-CD3 stimulation in control subjects (FIG. 1), whereas no induction was observed in PBMC collected from at-risk individuals.

Example 2: Subjects with Active RA have Impaired Induction of PTPN22 in PBMC after Anti-CD3 Antibody Stimulation Experiments were also performed to determine if the impaired induction of PTPN22 can also be observed in PBMC samples collected from active RA patients and if the impaired induction of PTPN22 can be reversed after an effective treatment.

Figure 2:
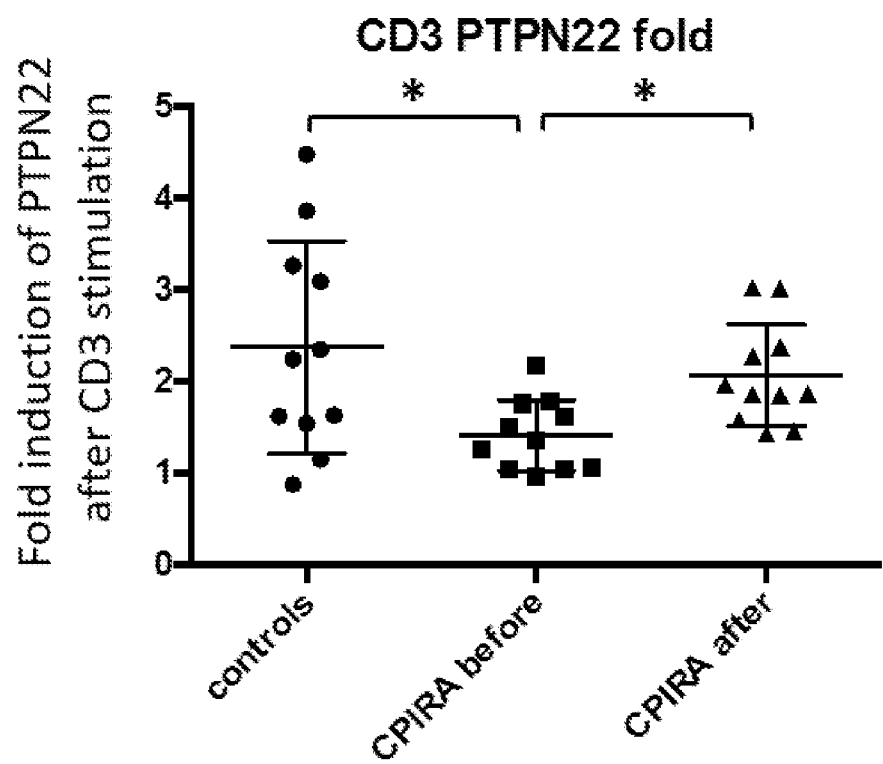
FIG. 2. Normalization of anti-CD3 antibody mediated induction of PTPN22 after effective treatments.

Active RA patients were recruited through the Central Pain in Rheumatoid Arthritis (CPIRA) study. The PBMC were collected from active RA patients at the time when they switched or started a new RA treatment and were also collected 12 weeks after the treatment started. The impaired anti-CD3 antibody mediated induction of PTPN22 was observed in PBMC of active RA patients and was corrected after 12 weeks of an effective treatment (FIG. 2).

Figure 3:
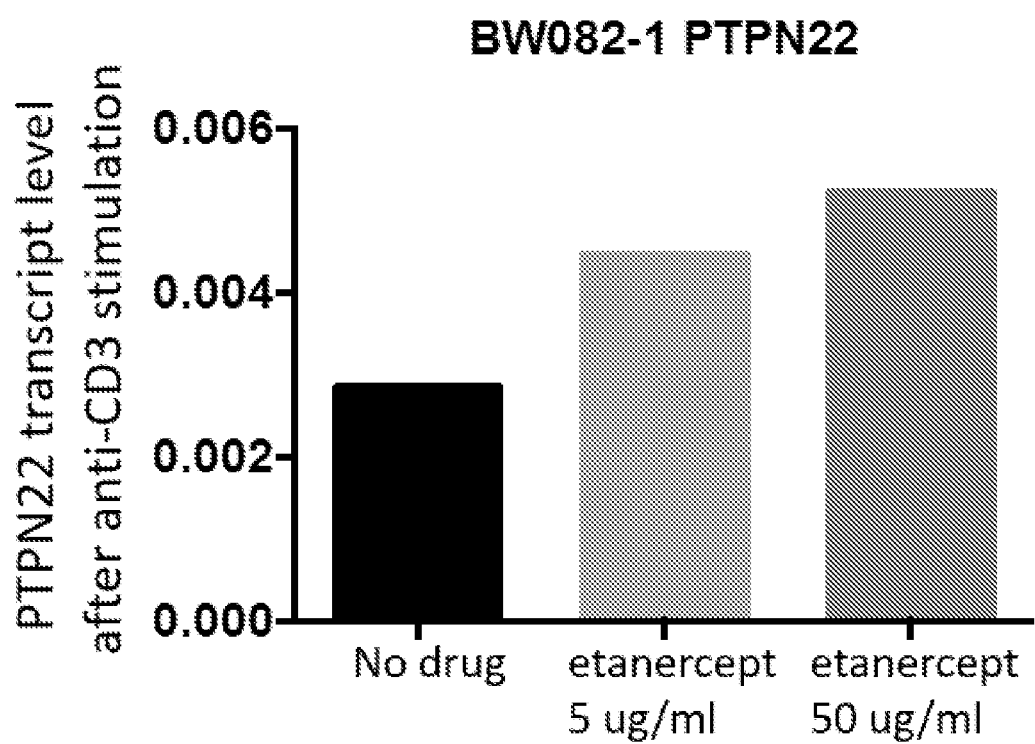
FIG. 3. Normalization of anti-CD3 antibody mediated induction of PTPN22 in the presence of etanercept.

Example 3: Anti-CD3 Antibody Induced Expression Level of PTPN22 in PBMC in the Presence of Etanercept and Adalimumab Indicates Responsiveness to Treatment The anti-CD3 antibody induced expression of PTPN22 in PBMC of an active RA patient was enhanced by etanercept (ENBREL®), an inhibitor of TNFa, in vitro in a dose-dependent manner (FIG. 3). It was therefore postulated that the in vitro reversibility by TNFa inhibitors, such as etanercept and adalimumab (HUMIRA®) was correlated with patient's response to the drugs and was a reliable predictor of clinical response.

PBMC collected from 14 CPIRA subjects before they started either etanercept or adalimumab were analyzed (Table 1). Seven of the ten subjects were treated by etanercept. Four responded to etancercept, and three did not respond.

The remaining seven patients were treated by adalimumab (five responded and two did not respond to the treatment). One of the adalimumab non-responders (BW34) also had a history of non-response to etanercept before entering CPIRA study.

The responsiveness to treatment was determined by the following definition.

CDAI decrease>=12 for those with baseline CDAI>22,
CDAI decrease>=6 for those with baseline CDAI>=10,
CDAI decrease>=1 for those with baseline CDAI<10.

PBMCs (1 million cells) of these subjects that were collected before the treatment were stimulated in vitro with anti-CD3 antibodies (2.5 ug/ml) in the absence or presence of corresponding drug (etanercept 250 ug/ml, adalimumab 100 ug/ml) for 24 hours. PBMC from subject BW34 was tested separately with etancercept and adalimumab. RNA was harvested from the stimulated cells and the level of PTPN22 transcripts was quantified with RT-PCR.

Figure 4:
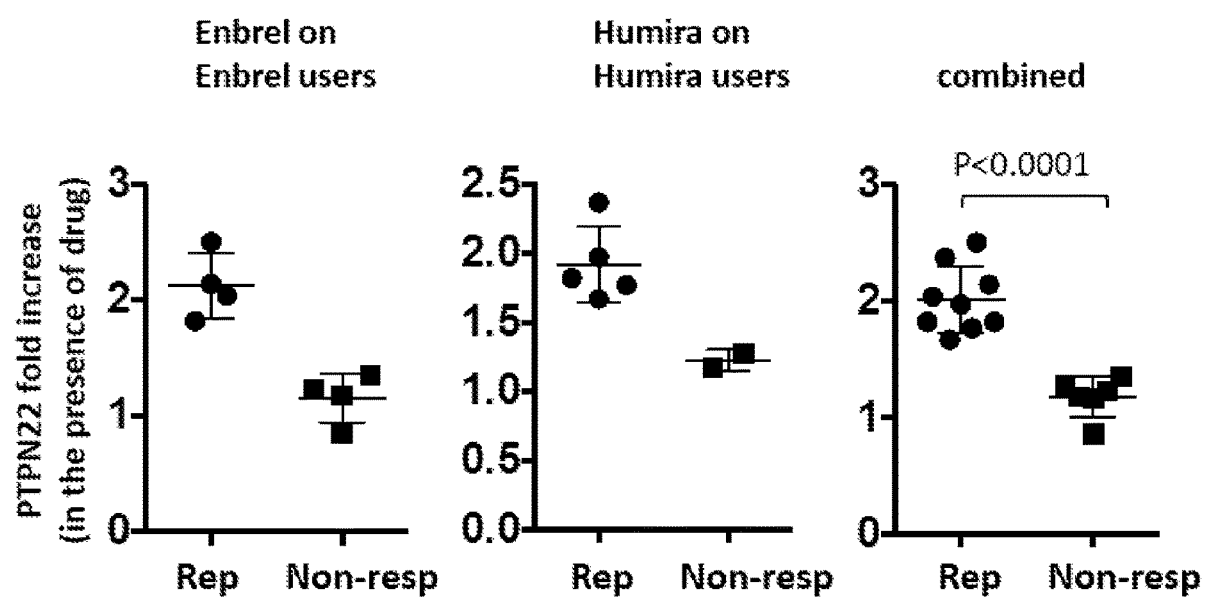
FIG. 4. Anti-CD3 antibody mediated induction of PTPN22 in PBMCs from responders and non-responders to etanercept (ENBREL®) and/or adalimumab (HUMIRA®).

The PTPN22 level from cells stimulated in the presence of drug was then divided by the level obtained from cells stimulated in the absence of drug. This drug/no-drug ratio calculated from the 9 drug responders ranged from 1.67 to 2.5, whereas the ratio calculated from the 6 drug non-responders ranged from 0.86 to 1.35 (FIG. 4 and Table 1).

The p value between responders and non-responders was 0.0002 in two-tailed Student's t test.

TABLE 1

|  |  | 1st visit CDAI | 2nd visit CDAI | ΔCDAI | PTPN22 Drug/no-drug ratio |
| --- | --- | --- | --- | --- | --- |
| Etanercept Responder | BW39 | 12.5 | 0 | 12.5 | 2.14 |
|  | BW56 | 19 | 6.5 | 12.5 | 2.04 |
|  | BW82 | 15 | 6 | 9 | 1.82 |
|  | BW110 | 35 | 12 | 23 | 2.5 |

TABLE 1-continued

|  |  | 1st visit CDAI | 2nd visit CDAI | ΔCDAI | PTPN22 Drug/no-drug ratio |
| --- | --- | --- | --- | --- | --- |
| Etanercept Non-responder | BW53 | 27 | 25.5 | 1.5 | 0.86 |
|  | BW80 | 21 | 21.5 | −0.5 | 1.18 |
|  | BW116 | 29 | 23 | 6 | 1.23 |
|  | BW34* |  |  |  | 1.35 |
| adalimumab Responder | BW32 | 15.2 | 0 | 15.2 | 1.82 |
|  | BW57 | 19 | 9 | 10 | 1.77 |
|  | BW85 | 46 | 25 | 21 | 1.97 |
|  | BW89 | 57 | 34 | 23 | 2.37 |
|  | BS137 | 31 | 18 | 13 | 1.67 |
| adalimumab Non-responder | BW34 | 29 | 24.2 | 4.8 | 1.17 |
|  | BW83 | 14 | 13 | 1 | 0.93 |

*Subject BW34 did not respond to etanercept before entering CPIRA study. The CDAI scores before and after etanercept treatment were not recorded.

Figure 5:
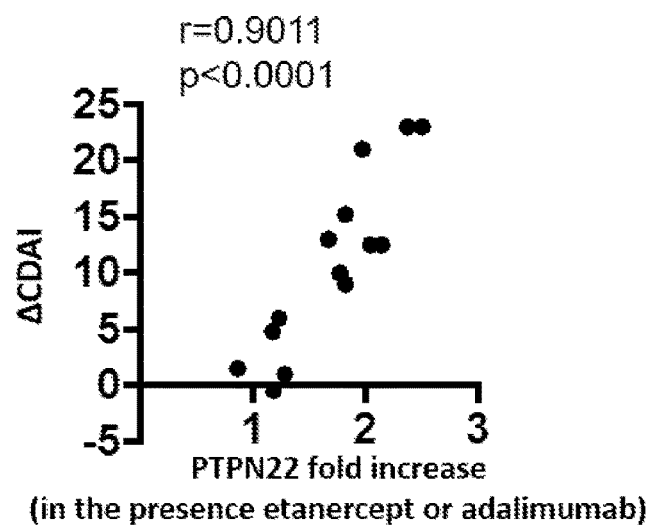
FIG. 5. Anti-CD3 antibody mediated induction of PTPN22 in the presence of etanercept and adalimumab correlates with clinical disease activity index (CDAI) change.

FIG. 5 further shows anti-CD3 antibody mediated induction of PTPN22 in the presence of etanercept and adalimumab correlates with clinical disease activity index (CDAI) change due to the treatment.

Example 4: Anti-CD3 Antibody Induced Expression Level of PTPN22 in PBMC in the Presence of Tofacitinib Indicates Responsiveness to Treatment Experiments were performed to determine whether anti-CD3 antibody induced alterations in expression level of PTPN22 in PBMC in the presence of tofacitinib indicated responsiveness to treatment.

PBMCs (at least 1 million cells) of these subjects that were collected before the treatment were stimulated in vitro with anti-CD3 antibodies (2.5 ug/ml) in the absence or presence of tofacitinib for 24 hours. RNA was collected from the stimulated cells and the level of PTPN22 transcripts was quantified with RT-PCR.

The responsiveness to treatment was determined by the methods as described in Example 3.

Figure 6:
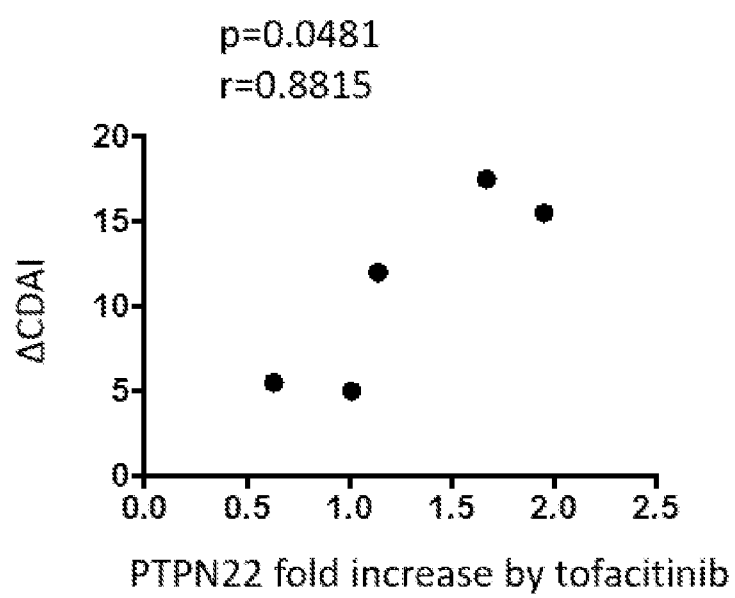
FIG. 6. Anti-CD3 antibody mediated induction of PTPN22 in the presence of tofacitinib correlates with CDAI change.

The PTPN22 level from cells stimulated in the presence of drug were then divided by the level obtained from cells stimulated in the absence of drug. The drug/no-drug ratio was correlated with responsiveness to the treatment (FIG. 6).

Example 5: Anti-CD3 Antibody Induced Expression Level of PFKFB3 and ATM in PBMC in the Presence of Etanercept (ENBREL®) or Adalimumab (HUMIRA®) Indicates Responsiveness to Drug Experiments were performed to determine whether the anti-CD3 antibody-induced changes in expression level of PFKFB3 and ATM in PBMC in the presence of a drug indicate responsiveness to the drug.

PBMCs (at least 1 million cells) of subjects with RA were collected before the treatment, and then were stimulated in vitro with anti-CD3 antibodies (2.5 ug/ml) in the absence or presence of etanercept (ENBREL®) or adalimumab (HUMIRA®) for 24 hours. RNA was collected from the stimulated cells and the levels of PFKFB3 and ATM transcripts were quantified with RT-PCR. The responsiveness to treatment was determined by the definitions as described in Example 3.

The transcript level of PFKFB3 or ATM from cells stimulated in the presence of drug was then divided by the level obtained from cells stimulated in the absence of drug (FIGS. 7A and 7B). The drug/no-drug ratio indicated responsiveness to the drug.

Figure 8A:
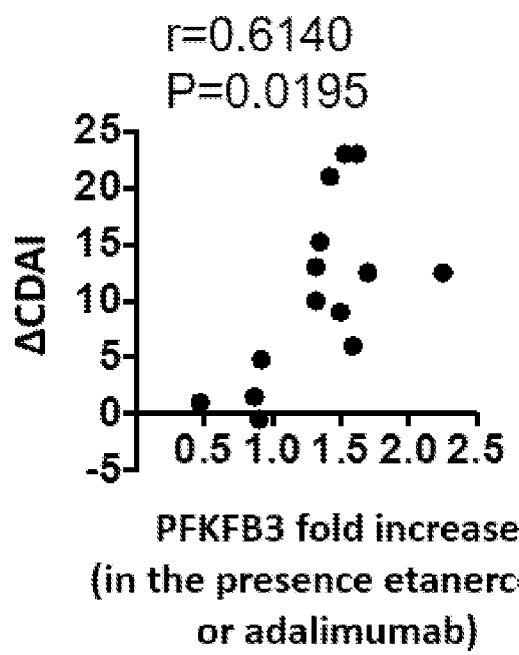
FIG. 8A. Anti-CD3 antibody mediated induction of PFKFB3 in the presence of adalimumab correlates with CDAI change.
Figure 8B:
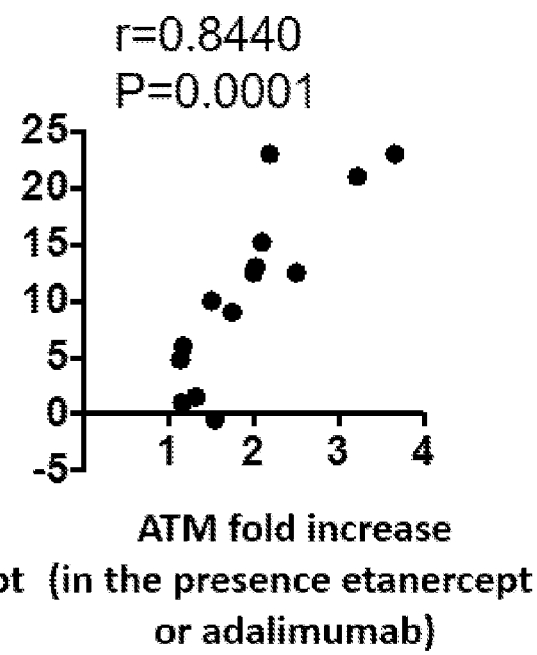
FIG. 8B. Anti-CD3 antibody mediated induction of ATM in the presence of adalimumab correlates with CDAI change.

FIGS. 8A and 8B further show anti-CD3 antibody mediated induction of PFKFB3 or ATM in the presence of etanercept and adalimumab correlates with clinical disease activity index (CDAI) change due to the treatment.

Example 6: Anti-CD3 Antibody Induced Expression Level of PTPN22 in PBMC in the Presence of Methotrexate and Tocilizumab Indicates Responsiveness to Treatment Experiments are performed to determine whether the anti-CD3 induced expression level of PTPN22 in PBMC in the presence of methotrexate and tocilizumab (ACTEMRA®, an IL-6R antibody) indicates responsiveness to treatment.

PBMC collected from subjects before the treatment starts are analyzed. The first group of subjects are then treated by methotrexate. The second group of subjects are then treated by tocilizumab. The third group are then treated by the combination of methotrexate and tocilizumab. The responsiveness to treatment can be determined by the definitions as described in Example 3.

PBMCs (at least 1 million cells) of these subjects that are collected before the treatment are stimulated in vitro with anti-CD3 antibodies (2.5 ug/ml) in the absence or presence of corresponding drug (methotrexate, tocilizumab, or the combination of methotrexate and tocilizumab) for 24 hours. RNA is collected from the stimulated cells and the level of PTPN22 transcripts is quantified with RT-PCR.

The PTPN22 level from cells stimulated in the presence of drug are then divided by the level obtained from cells stimulated in the absence of drug. It is expected that the drug/no-drug ratio is correlated with responsiveness to the treatment.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
   (i) providing a sample comprising peripheral blood mononuclear cells (PBMCs) or T cells collected from a subject;
   (ii) contacting the sample with an anti-CD3 antibody in the presence of a test compound; and
   (iii) measuring the expression or transcript levels of one or more RA-related genes selected from the group consisting of protein tyrosine phosphatase non-receptor 22 (PTPN22), 6-phosphofructo-2-kinase/fructose-2,6-bisphosphatase 3 (PFKFB3), and ataxia telangiectasia mutated (ATM).

2. The method of claim 1, wherein the one or more RA-related genes comprises PTPN22.

3. The method of claim 1, wherein the one or more RA-related genes comprises PFKFB3.

4. The method of claim 1, wherein the one or more RA-related genes comprises ATM.

5. The method of claim 1, wherein the test compound is an antibody.

6. The method of claim 1, wherein the test compound is a small molecule.

7. The method of claim 1, wherein the test compound is etanercept, adalimumab, tofacitinib, baricitinib, methotrexate, tocilizumab, sarilumab, golimumab, infliximab, certolizumab, or abatacept.

* * * * *